United States Patent
Prasad et al.

(10) Patent No.: US 6,849,613 B2
(45) Date of Patent: Feb. 1, 2005

(54) MULTIPLE ANTIOXIDANT MICRONUTRIENTS

(76) Inventors: Kedar N. Prasad, 351 Fairfax St., Denver, CO (US) 80220; Gerald M. Haase, 5655 S. Grape Ct., Greenwood Village, CO (US) 80121

( * ) Notice: Subject to any disclaimer, the term of this patent is extended or adjusted under 35 U.S.C. 154(b) by 249 days.

(21) Appl. No.: 10/229,271

(22) Filed: Aug. 28, 2002

(65) Prior Publication Data

US 2003/0147996 A1 Aug. 7, 2003

Related U.S. Application Data

(60) Provisional application No. 60/315,523, filed on Aug. 29, 2001.

(51) Int. Cl.$^7$ ................. A61K 31/70; A61K 31/555; A61K 31/59; A61K 31/525; A61K 31/355
(52) U.S. Cl. ................. 514/52; 514/188; 514/167; 514/251; 514/458; 514/474; 514/494; 514/574; 514/725
(58) Field of Search ................. 514/52, 188, 167, 514/251, 458, 474, 494, 574, 725

(56) References Cited

U.S. PATENT DOCUMENTS

| | | | | |
|---|---|---|---|---|
| 2,939,821 A | * | 6/1960 | Eigen et al. ................ | 514/52 |
| 3,446,899 A | * | 5/1969 | Louis et al. ................ | 514/474 |
| 3,584,114 A | * | 6/1971 | Cavalli ...................... | 424/465 |
| 3,777,029 A | * | 12/1973 | Magrid ...................... | 514/356 |
| 4,740,373 A | * | 4/1988 | Kesselman et al. ........ | 424/638 |
| 5,571,441 A | * | 11/1996 | Andon et al. .............. | 252/1 |
| 5,976,568 A | * | 11/1999 | Riley ......................... | 424/451 |
| 5,985,339 A | * | 11/1999 | Kamarei .................... | 426/72 |
| 6,451,341 B1 | * | 9/2002 | Slaga et al. ................ | 424/468 |

* cited by examiner

Primary Examiner—Raymond J. Henley, III
(74) Attorney, Agent, or Firm—Ostrolenk, Faber, Gerb & Soffen, LLP

(57) ABSTRACT

A method for administering an antioxidant composition to humans according to their age and sex is disclosed wherein the method comprises administering to said humans a daily dose of a multiple antioxidant micronutrient composition comprising vitamin A (palmitate), beta carotene (from natural d. salina), vitamin C (calcium ascorbate), vitamin D-3 (cholecalciferol), natural source vitamin E including both d-alpha tocopheryl and d-alpha tocopheryl acid succinate, thiamine mononitrate, riboflavin, niacinamide ascorbate, d-calcium pantothenate, pyridoxine hydrochloride, cyanocobalamin, folic acid (folacin), d-biotin, selenium (1-seleno methionine), chromium picolinate, zinc glycinate, calcium citrate, and magnesium citrate. For persons over the age of about 51, the composition preferably further comprises one or more of co-enzyme $Q_{10}$, N-acetyl cysteine, and alpha lipoic acid. Preferably, also, vitamin D is added for women over the age of about 36.

16 Claims, No Drawings

MULTIPLE ANTIOXIDANT MICRONUTRIENTS

We claim the benefit under Title 35, United States Code, §120 of U.S. Provisional Application No. 60/315,523, filed Aug. 29, 2001, entitled MULTIPLE ANTIOXIDANT MICRONUTRIENTS FOR OPTIMAL HEALTH.

BACKGROUND OF THE INVENTION

In the beginning, the earth's atmosphere had no oxygen. Anaerobic organisms, which can live without oxygen, were thriving. About 2.5 billion years ago, blue-green algae in the ocean acquired the ability to split water into hydrogen and oxygen and this chemical reaction initiated the release of oxygen into the atmosphere. The increased levels of atmospheric oxygen caused extinction of many anaerobic organisms owing to oxygen's toxicity. This important biological event also led to the evolution of multicellular organisms, including humans, who utilize oxygen for survival. The content of oxygen in the air gradually increased to the current amounts of about 21 percent in dry air and about 34 percent in water. The use of oxygen by any organism generates free radicals that are toxic. Therefore, during this period of atmospheric oxygenation, organisms must have struggled to survive the sudden exposure to oxygen toxicity. There must have been enormous rearranging of nucleotides in genes to produce specific proteins that could protect organisms against the damage produced by free radicals.

This process eventually led to the production of three antioxidant enzymes. Superoxide dismutase (SOD) requires manganese, copper, or zinc for its biological activity. Mn-SOD is present in mitochondria, whereas Cu-SOD and Zn-SOD are present in the cytoplasm and nucleus of the cell. All three can destroy free radicals and hydrogen peroxide. Another enzyme, catalase, requires iron for its biological activity and it destroys $H_2O_2$ in cells. Human tissue also contains glutathione peroxidase which requires selenium for its biological activity. It is also responsible for removing hydrogen peroxide.

Although iron, copper, and manganese are essential for the activities of antioxidant enzymes, a slight excess of free iron, Cu, or Mn can increase the production of free radicals, and subsequently enhance the risk of various chronic diseases. In addition, organisms, including mammals, consume certain antioxidants that are needed for growth and survival from plant sources. These antioxidants include carotenoids, vitamins A, C, and E, flavonoids, polyphenols, and herbal antioxidants.

Currently, the doses of antioxidants for the greatest benefit to human health are not well established. Nevertheless, increasing numbers of people are taking some form of supplements in the hope that it will optimize their health. Unfortunately, at present, they rely on advice from health-related magazines, books, advertising, radio and television reports or vitamin store salespeople. In fact, most people consume these nutrients without any scientific rationale. Furthermore, the majority of vitamin/mineral preparations have not given adequate attention to the dose, type, and chemical form of antioxidants, and appropriate minerals and other micronutrients.

SUMMARY OF THE INVENTION

The present invention is directed to a method for optimizing the health of humans according to their age and sex comprising administering to said humans a daily dose of a multiple antioxidant micronutrient composition comprising vitamin A (palmitate), beta-carotene (from natural d. salina), vitamin C (calcium ascorbate), vitamin D-3 (cholecalciferol), natural source vitamin E including both d-alpha tocopherol and d-alpha tocopheryl acid succinate, thiamine mononitrate, riboflavin, niacinamide ascorbate, d-calcium pantothenate, pyridoxine hydrochloride, cyanocobalamin, folic acid (folacin), d-biotin, selenium (l-seleno methionine), chromium picolinate, zinc glycinate, calcium citrate, and magnesium citrate.

For persons over the age of about 51, the composition preferably further comprises one or more of co-enzyme $Q_{10}$, N-acetyl cysteine, and alpha lipoic acid. Preferably, also, vitamin D is added for women over the age of about 36.

DESCRIPTION OF THE PREFERRED EMBODIMENTS

Generally healthy patients on an optimal preventive health formula are routinely categorized by age and sex, i.e., Ages 13 to 17 years, male and female;
Ages 18 to 35 years, male and female;
Ages 36 to 50 years, male;
Ages 36 to 50 years, female;
Ages 51 to 65 years, male;
Ages 51 to 65 years, female;
Ages 66 and over, male; and
Ages 66 and over, female.

Most commercially available multiple supplement formulations contain iron, copper, and/or manganese. It is well known that these substances actively generate free radicals when combined with vitamin C. In addition, these minerals are more easily absorbed from the intestinal tract in the presence of antioxidants, such as vitamin C, and thereby increase the body stores of these minerals. Increased iron stores have been associated with many chronic human conditions, including heart disease, cancer, and neurological diseases. Therefore, the addition of iron, copper, or manganese to any multiple antioxidant preparation has no scientific merit for optimal health or disease prevention. Only in cases where a person has iron-deficiency anemia, is a short-term iron supplement essential.

Many commercially available preparations contain heavy metals such as boron, vanadium, and molybdenum. Sufficient amounts of these metals are obtained from the diet and the daily consumption of excess amounts over a long period of time can be neurotoxic.

Many commercial preparations contain inositol, methionine, and choline in varying amounts, e.g., 30 mg to 60 mg. These small doses serve no useful purpose for improving health because 400 mg to 1000 mg of these nutrients are obtained daily from even the most minimal diet.

Para-aminobenzoic acid (PABA) is present in some multiple vitamin preparations. PABA has no biologic function in mammalian cells and can block the antibacterial effect of sulfonamides. Therefore, the effectiveness of a sulfonamide may be reduced in some patients being treated for a bacterial infection.

Commercially sold multiple antioxidant preparations often contain varying amounts of N-acetyl cysteine or alpha lipoic acid. These nutrients are utilized because they are known to increase glutathione levels in the cells. Reduced glutathione is a powerful antioxidant and actively protects both normal and cancer cells against radiation damage. Many cancer patients take antioxidant supplements without the knowledge of their oncologists. Therefore, the consumption of antioxidant preparations containing N-acetyl cysteine or alpha lipoic acid by these patients undergoing radiation therapy could interfere with important anti-cancer treatment.

The addition of both beta-carotene and vitamin A to any multiple vitamin preparation is essential, because beta-carotene not only acts as a precursor of vitamin A, but also performs important biological functions that cannot be performed by vitamin A. Beta-carotene increases the expression of the connexin gene, which codes for a gap junction protein that is necessary for maintaining the normal cellular phenotype. While other carotenoids, such as lycopene, xanthophylls, and lutein, are also important for health, they can be obtained from an adequate diet with tomato (lycopene), spinach (lutein), and paprika (xanthophylls) in amounts that are higher than those that can be supplied from supplements. Therefore, the addition of a few milligrams of lycopene, xanthophylls, and lutein to any multiple vitamin preparation serves no useful purpose for health or disease prevention.

The proper ratio of two forms of vitamin E, d-alpha tocopherol, which is normally present in the body, and d-alpha tocopheryl succinate, to a multiple antioxidant preparation is essential. Alpha tocopheryl succinate is the most effective form of vitamin E inside the cells, whereas alpha tocopherol can readily act as an antioxidant in the intestinal tract and in the extracellular environment of the body. Alpha-tocopherol at doses of 20–60 μg/ml can stimulate the immune system, while the beta, gamma, and delta forms at similar doses can inhibit immune system. This effect of these forms of tocopherol may not be related to their antioxidant action and, since they are less effective than alpha tocopherol, their supplementation is not recommended.

Tocotrienols are also antioxidants, but they may inhibit cholesterol synthesis. Since this activity is not beneficial in healthy individuals, prolonged consumption of tocotrienols as a supplement is not optimal.

Vitamin C is usually administered as ascorbic acid, which can cause stomach upset, diarrhea, and other complications in some individuals. However, using the calcium ascorbate form is most suitable because it is non-acidic and has not been shown to produce negative side effects. The use of potassium ascorbate and magnesium ascorbate in any multiple vitamin preparation is unnecessary. Also, any multiple micronutrient preparation should include adequate amounts of B-vitamins (2–3 times of RDA) and appropriate minerals.

A supplement that attempts to include all antioxidants or micronutrients without regard to age, sex, general health and disease status, is irrational and cannot be recommended. It appears more appropriate to utilize a basic antioxidant formulation that contains the necessary nutrients for optimal health, and then supplement that product with additional nutrients based on the above individual factors.

A balanced diet may be sufficient for normal growth, but supplemental micronutrients, including antioxidants, are important for optimal health. With the current typical American diet, one would have difficulty eating fresh fruit and vegetables daily in the amounts and at the frequencies each day necessary to maintain sustained optimal levels of beta-carotene and vitamins A, C, and E in body tissues. In addition, when one travels away from home, the availability of these vital foods may be limited. While some scientists believe that a balanced diet is sufficient for maintaining optimal health, many studies suggest that most foods contain naturally occurring toxic, as well as protective, substances. While a balanced diet may prevent vitamin deficiency, it may not be sufficient for disease prevention since the concept of "balance" may vary markedly from one individual to another. In addition, environmental sources of toxins (such as pesticides) may well vary from region to region.

Another advantage of the supplements of the present invention is that they can be consumed at the most appropriate time to maximize their effectiveness in preventing the formation of toxic chemicals (mutagens and carcinogens) in the gastrointestinal tract during digestion. For example, if vitamins C and E are taken immediately before eating nitrite-rich food, the formation of mutagenic nitrosamines in the stomach may be reduced, whereas taking these vitamins a few hours after such a meal may not be effective in reducing the formation of this cancer-causing substance. Furthermore, studies have demonstrated that levels of fecal mutagens (a possible source of cancer) in people who regularly eat meat are much higher than in vegetarians. Ingestion of vitamins C and E has been shown to reduce the levels of mutagens in the feces. Therefore, these supplements should be taken before, or right after, eating meat, whereas consuming them several hours after such a meal may not be as effective.

The risk of chronic illnesses may depend upon the relative consumption of protective versus toxic substances. If the daily intake of protective substances is higher than toxic agents, the incidence of chronic illness may be reduced. Since we know very little about the relative levels of toxic and protective substances in any diet, a daily supplement of micronutrients including antioxidants would assure a higher level of preventive protection.

Free radicals are examples of primary agents involved in increasing the risk of cancer, heart disease, and neurological disease. If they damage normal dividing cells, the risk of cancer is increased. If they damage non-dividing cells, such as neurons, the risk of neurological diseases is enhanced. Therefore, quenching free radicals with antioxidants is important for the maintenance of optimal health.

The basic micronutrient formulation of the present invention satisfies all of the required components previously outlined and provides a foundation for a maximally effective preventive formula for otherwise healthy people. Since the biological half-life of most micronutrients is much less than 12 hours, it is essential to take these supplements twice a day.

In older age groups (greater than 50 years), the addition of co-enzyme $Q_{10}$ is important because it may improve mitochondrial function and increase energy level. In addition, the likelihood of mitochondrial damage increases with age.

Furthermore, the sulfhydryl compounds, such as glutathione, are important antioxidants that protect cells against free radical damage. Although glutathione levels decrease with aging, it cannot be taken as a supplement because it is completely destroyed during digestion. Therefore, N-acetyl cysteine and alpha lipoic acid, which increase cellular levels of glutathione, are recommended for older individuals.

To reduce the risk of osteoporosis in women, an appropriate calcium/magnesium preparation with vitamin D is required. The citrate form is most efficiently absorbed where as the oxide form is not. The presence of vitamin D increases the absorption of calcium from the intestinal tract. This supplementation is especially important after menopause where the loss of calcium increases with age.

Suggested Daily Formulation

Ages 13–17 Years, Male and Female

| | |
|---|---|
| vitamin A (palmitate) | 2,500 I.U. |
| beta-carotene (from natural *d. salina*) | 7.5 mg |
| vitamin C (calcium ascorbate) | 250 mg |
| vitamin D-3 (cholecalciferol) | 200 I.U. |
| natural source vitamin E | |
| (d-alpha tocopherol) | 50 I.U. |
| (d-alpha tocopheryl acid succinate) | 50 I.U. |
| thiamine mononitrate | 2 mg |
| riboflavin | 2.5 mg |
| niacinamide ascorbate | 15 mg |
| d-calcium pantothenate | 5 mg |
| pyridoxine hydrochloride | 2.5 mg |
| cyanocobalamin | 5 μg |
| folic acid (folacin) | 400 μg |
| d-biotin | 100 μg |
| selenium (l-seleno methionine) | 50 μg |
| chromium picolinate | 25 μg |
| zinc glycinate | 7.5 mg |
| calcium citrate | 125 mg |
| magnesium citrate | 62.5 mg |

Ages 18–35 Years, Male and Female

| | |
|---|---|
| vitamin A (palmitate) | 5,000 I.U. |
| beta-carotene (from natural *d. salina*) | 15 mg |
| vitamin C (calcium ascorbate) | 500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 100 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |

Ages 36–50 Years, Male

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 μg |
| d-biotin | 200 μg |
| selenium (l-seleno methionine) | 100 μg |
| chromium picolinate | 50 μg |

-continued

| | |
|---|---|
| zinc glycinate | 15 mg |
| calcium citrate | 250 mg |
| magnesium citrate | 125 mg |

For Women, the Following Supplements Should Be Added

| | |
|---|---|
| calcium citrate | 1,500 mg |
| magnesium citrate | 750 mg |
| vitamin D | 100 I.U. |

Ages 51–65 Years, Male

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |
| co-enzyme $Q_{10}$ | 30 mg |
| n-acetyl cysteine | 250 mg |

For Women, the Following Supplements Should Be Added

| | |
|---|---|
| calcium citrate | 1,500 mg |
| magnesium citrate | 750 mg |
| vitamin D | 100 I.U. |

Age 66 and Over, Male

| | |
|---|---|
| vitamin A (palmitate) | 5,000 I.U. |
| beta-carotene (from natural *d. salina*) | 15 mg |
| vitamin C (calcium ascorbate) | 2,500 mg |
| vitamin d-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |

-continued

| | |
|---|---|
| co-enzyme Q₁₀ | 30 mg |
| n-acetyl cysteine | 250 mg |
| alpha lipoic acid | 30 mg |

For Women, the Following Supplements Should Be Added

| | |
|---|---|
| calcium citrate | 1,500 mg |
| magnesium citrate | 750 mg |
| vitamin D | 100 I.U. |

It will be understood that, in addition to antioxidant micronutrients, diet and lifestyle recommendations from the healthcare professional are also very important in maintaining optimal health and preventing disease risk. For example, in the diet, one should increase consumption of fresh fruits and vegetables; increase consumption of fiber (26 grams per day) from fruits, vegetables, and fiber-rich cereals; reduce fat consumption to 20 percent of total calories (1 gram of fat equals nine calories); avoid excessive calories; reduce consumption of food with high nitrate or nitrite content (e.g. preserved meats) and whenever eating such foods, first consume antioxidants; avoid excessive amounts of charcoal-broiled or smoked meat or fish; reduce the consumption of pickled fruits and vegetables; reduce the consumption of caffeine containing beverages; and, for women age 36 and older, consume a calcium-rich diet.

Additionally, one should:
1. avoid drinking excessive amounts of alcohol;
2. NOT SMOKE or chew tobacco and should avoid exposure to second-hand smoke;
3. exercise 3 to 5 days a week for 30 minutes and, if doing aerobic exercise for 30 minutes or more, take antioxidant supplements beforehand;
4. adopt a lifestyle of reduced stress; and
5. avoid excessive sun exposure and use of UV light for skin tanning or hyperbaric oxygen "cocktails" for energy bursts.

What is claimed is:

1. A composition for administration to male and female humans in the age range of from about 13 to about 17 years consisting essentially of:

| | |
|---|---|
| vitamin A (palmitate) | 2,500 I.U. |
| beta-carotene (from natural *d. salina*) | 7.5 mg |
| vitamin C (calcium ascorbate) | 250 mg |
| vitamin D-3 (cholecalciferol) | 200 I.U. |
| natural source vitamin E | |
| (d-alpha tocopherol) | 50 I.U. |
| (d-alpha tocopheryl acid succinate) | 50 I.U. |
| thiamine mononitrate | 2 mg |
| riboflavin | 2.5 mg |
| niacinamide ascorbate | 15 mg |
| d-calcium pantothenate | 5 mg |
| pyridoxine hydrochloride | 2.5 mg |
| cyanocobalamin | 5 μg |
| folic acid (folacin) | 400 μg |
| d-biotin | 100 μg |
| selenium (l-seleno methionine) | 50 μg |
| chromium picolinate | 25 μg |
| zinc glycinate | 7.5 mg |
| calcium citrate | 125 mg; and |
| magnesium citrate | 62.5 mg. |

2. A composition for administration to male and female humans in the age range of from about 18 to about 35 years consisting essentially of:

| | |
|---|---|
| vitamin A (palmitate) | 5,000 I.U. |
| beta-carotene (from natural *d. salina*) | 15 mg |
| vitamin C (calcium ascorbate) | 500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 100 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg; and |
| magnesium citrate | 125 mg. |

3. A composition for administration to male humans in the age range of from about 36 to about 50 years consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg; and |
| magnesium citrate | 125 mg. |

4. A composition for administration to female humans in the age range of from about 36 to about 50 years consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 μg |

-continued

| | |
|---|---|
| d-biotin | 200 μg |
| selenium (l-seleno methionine) | 100 μg |
| chromium picolinate | 50 μg |
| zinc glycinate | 15 mg |
| calcium citrate | 1500 mg |
| magnesium citrate | 750 mg; and |
| vitamin D | 100 I.U.. |

5. A composition for administration to male humans in the age range of from about 51 to about 65 years consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |
| co-enzyme $Q_{10}$ | 30 mg; and |
| n-acetyl cysteine | 250 mg. |

6. A composition for administration to female humans in the age range of from about 51 to about 65 years consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 1500 mg |
| magnesium citrate | 750 mg |
| co-enzyme $Q_{10}$ | 30 mg |
| n-acetyl cysteine | 250 mg; and |
| vitamin D | 100 I.U.. |

7. A composition for administration to male humans of the age of about 66 and over consisting essentially of:

| | |
|---|---|
| vitamin A (palmitate) | 5,000 I.U. |
| beta-carotene (from natural *d. salina*) | 15 mg |
| vitamin C (calcium ascorbate) | 2,500 mg |
| vitamin d-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |
| co-enzyme $Q_{10}$ | 30 mg |
| n-acetyl cysteine | 250 mg; and |
| alpha lipoic acid | 30 mg. |

8. A composition for administration to female humans of the age of about 66 and over consisting essentially of:

| | |
|---|---|
| vitamin A (palmitate) | 5,000 I.U. |
| beta-carotene (from natural *d. salina*) | 15 mg |
| vitamin C (calcium ascorbate) | 2,500 mg |
| vitamin d-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 1500 mg |
| magnesium citrate | 750 mg |
| co-enzyme $Q_{10}$ | 30 mg |
| n-acetyl cysteine | 250 mg |
| alpha lipoic acid | 30 mg; and |
| vitamin D | 100 I.U.. |

9. A method for administering an antioxidant composition to male and female humans comprising administering to said humans in the age range of from about 13 to about 17 years a composition consisting essentially of:

| | |
|---|---|
| vitamin A (palmitate) | 2,500 I.U. |
| beta-carotene (from natural *d. salina*) | 7.5 mg |
| vitamin C (calcium ascorbate) | 250 mg |
| vitamin D-3 (cholecalciferol) | 200 I.U. |
| natural source vitamin E | |
| (d-alpha tocopherol) | 50 I.U. |
| (d-alpha tocopheryl acid succinate) | 50 I.U. |
| thiamine mononitrate | 2 mg |
| riboflavin | 2.5 mg |
| niacinamide ascorbate | 15 mg |
| d-calcium pantothenate | 5 mg |

-continued

| | |
|---|---|
| pyridoxine hydrochloride | 2.5 mg |
| cyanocobalamin | 5 µg |
| folic acid (folacin) | 400 µg |
| d-biotin | 100 µg |
| selenium (l-seleno methionine) | 50 µg |
| chromium picolinate | 25 µg |
| zinc glycinate | 7.5 mg |
| calcium citrate | 125 mg; and |
| magnesium citrate | 62.5 mg. |

10. A method for administering an antioxidant composition to male and female humans comprising administering to said humans in the age range of from about 18 to about 35 years a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 100 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 µg |
| folic acid (folacin) | 800 µg |
| d-biotin | 200 µg |
| selenium (l-seleno methionine) | 100 µg |
| chromium picolinate | 50 µg |
| zinc glycinate | 15 mg |
| calcium citrate | 250 mg; and |
| magnesium citrate | 125 mg. |

11. A method for administering an antioxidant composition to male humans comprising administering to said humans in the age range of from about 36 to about 50 years a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 µg |
| d-biotin | 200 µg |
| selenium (l-seleno methionine) | 100 µg |
| chromium picolinate | 50 µg |
| zinc glycinate | 15 mg |
| calcium citrate | 250 mg; and |
| magnesium citrate | 125 mg. |

12. A method for administering an antioxidant composition to female humans comprising administering to said humans in the age range of from about 36 to about 50 years a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 µg |
| d-biotin | 200 µg |
| selenium (l-seleno methionine) | 100 µg |
| chromium picolinate | 50 µg |
| zinc glycinate | 15 mg |
| calcium citrate | 1500 mg |
| magnesium citrate | 750 mg; and |
| vitamin D | 100 I.U.. |

13. A method for administering an antioxidant composition to male humans comprising administering to said humans in the age range of from about 51 to about 65 years a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 µg |
| folic acid (folacin) | 800 µg |
| d-biotin | 200 µg |
| selenium (l-seleno methionine) | 100 µg |
| chromium picolinate | 50 µg |
| zinc glycinate | 15 mg |
| calcium citrate | 250 mg |
| magnesium citrate | 125 mg |
| co-enzyme $Q_{10}$ | 30 mg; and |
| n-acetyl cysteine | 250 mg. |

14. A method for administering an antioxidant composition to female humans comprising administering to said humans in the age range of from about 51 to about 65 years a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |

-continued

| | |
|---|---|
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 1500 mg |
| magnesium citrate | 750 mg |
| co-enzyme $Q_{10}$ | 30 mg |
| n-acetyl cysteine | 250 mg; and |
| vitamin D | 100 I.U. |

15. A method for administering an antioxidant composition to male humans comprising administering to said humans of the age of about 66 and over a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 2,500 mg |
| vitamin d-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |
| co-enzyme $Q_{10}$ | 30 mg |

-continued

| | |
|---|---|
| n-acetyl cysteine | 250 mg; and |
| alpha lipoic acid | 30 mg. |

16. A method for administering an antioxidant composition to female humans comprising administering to said humans of the age of about 66 and over a composition consisting essentially of:

| | |
|---|---|
| vitamin A (palmitate) | 5,000 I.U. |
| beta-carotene (from natural *d. salina*) | 15 mg |
| vitamin C (calcium ascorbate) | 2,500 mg |
| vitamin d-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 1500 mg |
| magnesium citrate | 750 mg |
| co-enzyme $Q_{10}$ | 30 mg |
| n-acetyl cysteine | 250 mg |
| alpha lipoic acid | 30 mg; and |
| vitamin D | 100 I.U. |

* * * * *